US005736507A

United States Patent [19]
Boots et al.

[11] Patent Number: 5,736,507
[45] Date of Patent: Apr. 7, 1998

[54] PEPTIDES DERIVED FROM AUTOANTIGEN FOR USE IN IMMUNOTHERAPY OF AUTOIMMUE DISEASES

[75] Inventors: Anna Maria Helena Boots, Verlengde Torenstraat; Gijsbertus Franciscus Maria Verheijden, Heischouw, both of Netherlands

[73] Assignee: Akzo Nobel N.V., Arnhem, Netherlands

[21] Appl. No.: 619,645

[22] PCT Filed: Oct. 25, 1995

[86] PCT No.: PCT/EP95/04201

§ 371 Date: Mar. 25, 1996

§ 102(e) Date: Mar. 25, 1996

[87] PCT Pub. No.: WO96/13517

PCT Pub. Date: May 9, 1996

[30] Foreign Application Priority Data

Oct. 27, 1994 [EP] European Pat. Off. ............ 94203128
Apr. 7, 1995 [EP] European Pat. Off. ............ 95200886

[51] Int. Cl.$^6$ .................... A61K 38/03; A61K 38/17; C07K 4/00; C07K 14/435
[52] U.S. Cl. .................... 514/2; 424/185.1; 435/7.24; 435/29; 435/975; 514/12; 514/13; 514/14; 514/15; 530/324; 530/325; 530/326; 530/327; 530/328; 530/395
[58] Field of Search .................... 530/326, 328, 530/395, 403, 300, 324, 325, 327; 435/4, 7.1, 7.24, 29, 975; 424/184.1, 185.1, 277.1, 572; 514/2, 12, 14, 15, 13

[56] References Cited

U.S. PATENT DOCUMENTS 5,356,779 10/1994 Mozes et al. .................... 435/7.24

FOREIGN PATENT DOCUMENTS 63-23898   2/1988   Japan.
WO 9501995  1/1995   WIPO.

OTHER PUBLICATIONS

Mackay, IR. Diagnosis of Autoimmune Disease: Past and Present. in Autoimmune Disease: Aetiopathogenesis, Diagnosis and Treatment. Lydyard, PM et al. eds. Blackwell Science Ltd. Oxford. pp. 137–154, 1994.

Tisch, et al. Proc. Nat. Acad. Sci. (USA) 91: 437–438, Jan. 1994.

Harlow, E and Lane, D. eds. in Antibodies: A Laboratory Manual. Cold Spring Harbor Laboratory, Cold Spring Harbor, New York. p. 70, 1988.

Adams, E et al. Clin. Exp. Immunol. 94(3): 500–506, 1993.

B.E. Hakala et al., *Journal of Biological Chemistry*, 268:34:25803–25810, 1993.

P. Nyirkos et al., *Biochemical Journal*, 269:1:268–268, 1990.

Database WPI, Derwent Publications, Ltd, AN 88–068419, Week 10, 1988.

T. Furya et al., Database Strand, Genetics Computer Group Sequence, Feb. 01, 1988.

*Primary Examiner*—David Saunders
*Assistant Examiner*—F. Pierre VanderVegt
*Attorney, Agent, or Firm*—Mary E. Gormley

[57] ABSTRACT

The present invention relates to novel peptides derived from the autoantigen HC gp-39, said peptides comprising at least one of the amino acid sequences FGRSFTLAS (SEQ ID No. 1), FTLASSETG (SEQ ID No. 2), YDDQESVKS (SEQ ID No. 3) and FSKIASNTQ (SEQ ID No. 4). The peptides resemble MHC Class II restricted T-cell epitopes present on the autoantigen HC gp-39 in articular cartilage. HC gp-39 and said peptides can be used in antigen-specific treatment of articular cartilage destruction in autoimmune diseases to induce tolerance of the immune system. The autoantigen HC gp-39 and said peptides are also suitable to induce arthritis in non-human animals, preferably mice. The invention furthermore relates to pharmaceutical compositions comprising said autoantigen and/or said peptides, a diagnostic method for the detection of autoreactive T cells in a test sample and test kits to be used in said method.

10 Claims, 4 Drawing Sheets

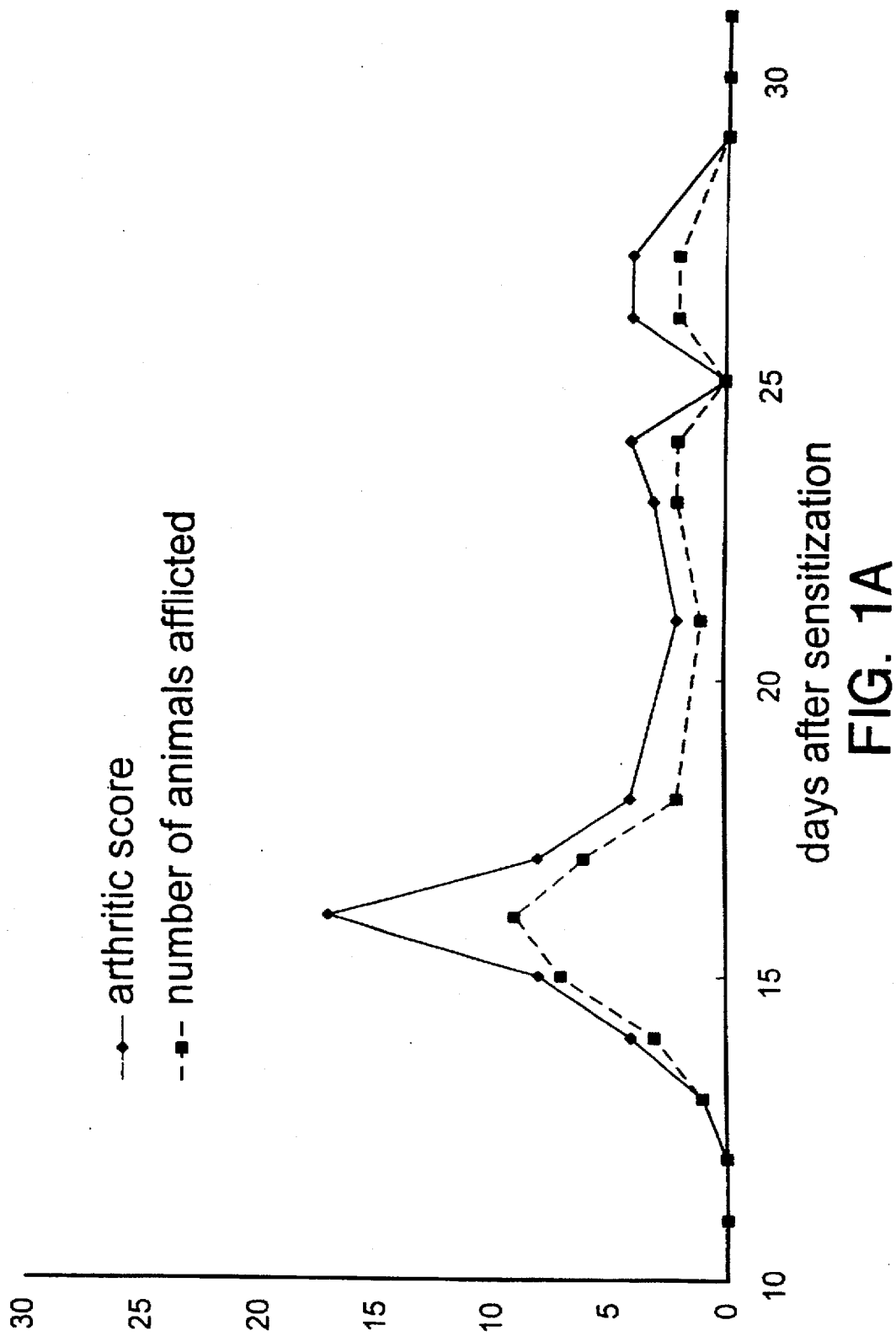

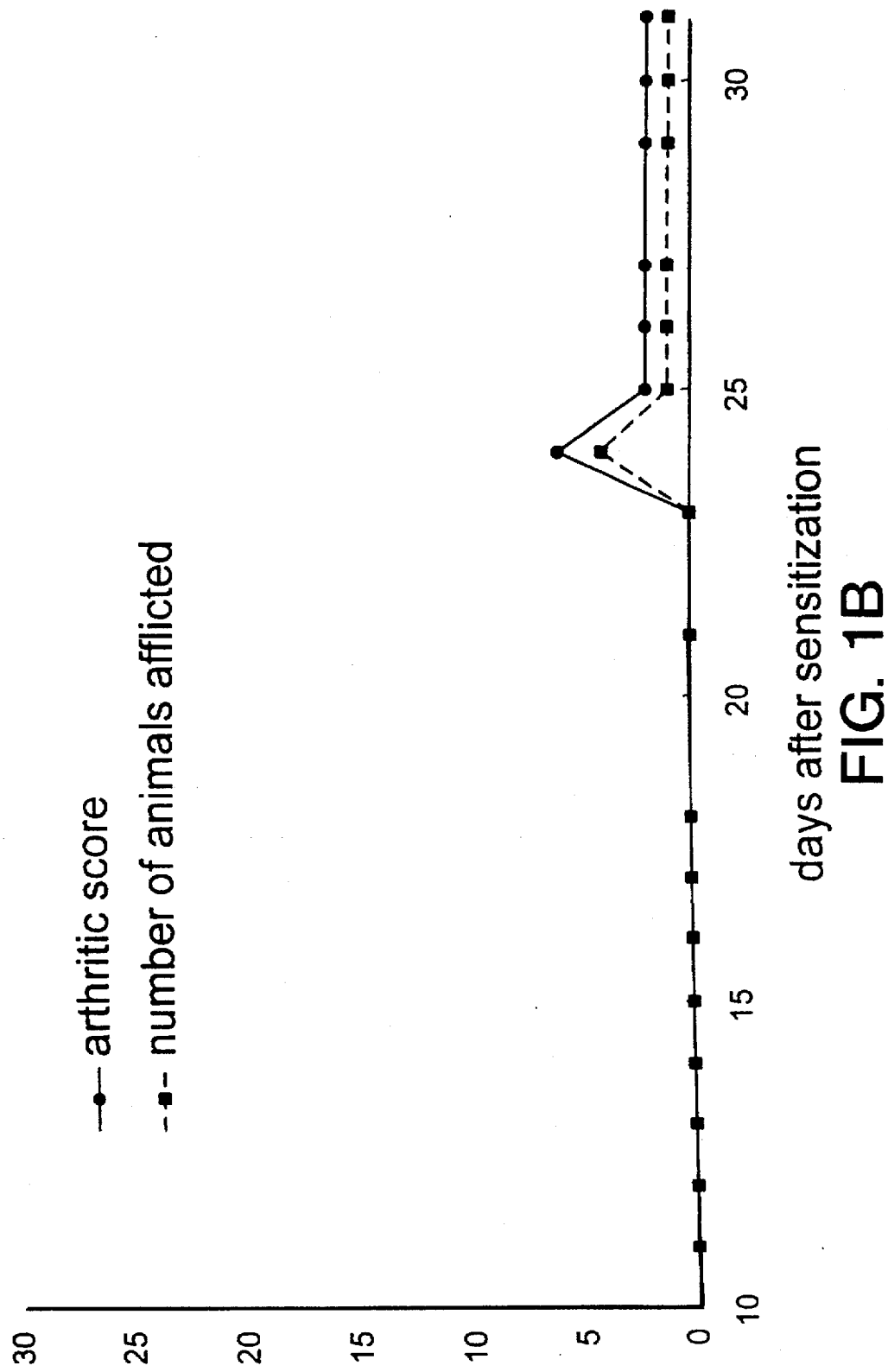

PEPTIDES DERIVED FROM AUTOANTIGEN FOR USE IN IMMUNOTHERAPY OF AUTOIMMUE DISEASES

FIELD OF THE INVENTION

The invention relates to a novel autoantigen and peptides derived thereof, their use in treatment of chronic destruction of articular cartilage in autoimmune diseases, pharmaceutical compositions comprising said peptides, a diagnostic method for the detection of autoreactive T cells in a test sample and test kits to be used in said method.

BACKGROUND OF THE INVENTION

The immune system is established on a principle of discrimination between foreign antigens (non-self antigens) and autoantigens (self antigens, derived from the individuals own body) achieved by a build in tolerance against the autoantigens.

The immune system protects individuals against foreign antigens and responds to exposure to a foreign antigen by activating specific cells such as T- and B lymphocytes and producing soluble factors like interleukins, antibodies and complement factors. The antigen to which the immune system responds is degraded by the antigen presenting cells (APCs) and a fragment of the antigen is expressed on the cell surface associated with a major histocompatibility complex (MHC) class II glycoprotein. The MHC-glycoprotein-antigen-fragment complex is presented to a T cell which by virtue of its T cell receptor recognizes the antigen fragment conjointly with the MHC class II protein to which it is bound. The T cell becomes activated, i.e. proliferates and/or produces interleukins, resulting in the expansion of the activated lymphocytes directed to the antigen under attack (Grey et al., Sci. Am., 261:38–46, 1989).

Self antigens are also continuously processed and presented as antigen fragments by the MHC glycoproteins to T cells (Jardetsky et al., Nature 353:326–329, 1991). Self recognition thus is intrinsic to the immune system. Under normal circumstances the immune system is tolerant to self antigens and activation of the immune response by these self antigens is avoided.

When tolerance to self antigens is lost, the immune system becomes activated against one or more self antigens, resulting in the activation of autoreactive T cells and the production of autoantibodies. This phenomenon is referred to as autoimmunity. As the immune response in general is destructive, i.e. meant to destroy the invasive foreign antigen, autoimmune responses can cause destruction of the body's own tissue.

The contribution of T cells to autoimmune diseases has been established by several studies. In mice, experimental autoimmune encephalomyelitis (EAE) is mediated by a highly restricted group of T cells, linked by their specificity for a single epitope of myelin basic protein (MBP) complexed to an MHC class II molecule. In the Lewis rat, a species with high susceptibility to various autoimmune diseases, disease has been shown to be mediated by T cells. In humans autoimmune diseases are also thought to be associated with the development of auto-aggressive T cells.

A destructive autoimmune response has been implicated in various diseases such as rheumatoid arthritis (RA), in which the integrity of articular cartilage is destroyed by a chronic inflammatory process resulting from the presence of large numbers of activated lymphocytes and MHC class II expressing cells. The mere presence of cartilage appears necessary for sustaining the local inflammatory response: it has been shown that cartilage degradation is associated with the activity of cartilage-responsive autoreactive T cells in RA (Sigall et al., Clin. Exp. Rheumat. 6:59, 1988; Glant et al., Biochem. Soc. Trans. 18:796, 1990; Burmester et al., Rheumatoid arthritis Smolen, Kalden, Maini (Eds) Springer-Verlag Berlin Heidelberg, 1992). Furthermore, removal of cartilage from RA patients by surgery was shown to reduce the inflammatory process (G. S. Panayi et al, Clin. Exp. Rheumatol. 11(suppl.8): S1–S8, 1993). The cartilage proteins are therefore considered to be target autoantigens which are competent of stimulating T cells. Activation of these autoreactive T cells leads to development of autoimmune disease.

The inflammatory response resulting in the destruction of the cartilage can be treated by several drugs, such as for example steroid drugs. However, these drugs are often immunosuppressive drugs that are nonspecific and have toxic side effects. The disadvantages of nonspecific immunosuppression makes this a highly unfavourable therapy.

The antigen-specific, nontoxic immunosuppression therapy provides a very attractive alternative for the non-specific immunosuppression. This antigen-specific therapy involves the treatment of patients with the target autoantigen or with synthetic T cell-reactive peptides derived from the autoantigen. These synthetic peptides correspond to T cell epitopes of the autoantigen and can be used to induce specific T cell tolerance both to themselves and to the autoantigen. Although it seems paradoxical to desensitize the immune system with the very same antigen responsible for activating the immune system, the controlled adminstration of the target (auto)antigen can be very effective in desensitization of the immune system.

To effectively use the tolerance therapy to treat the T cell mediated cartilage destruction, there is a great need to identify the responsible autoantigen and to find T cell-reactive peptides which can desensitize patients against the autoantigen that is activating the T cells responsible for the inflammatory process.

It is an object of the invention to provide the autoantigen and T cell reactive peptides derived from said autoantigen which are able to induce specific T cell tolerance to the responsible cartilage antigen in patients suffering from T cell-mediated cartilage destruction. It is another object of the invention to provide a method for detecting autoreactive T cells involved in the destruction of articular cartilage and test kits to be used in said method.

SUMMARY OF THE INVENTION

It was surprisingly found that Human Cartilage glycoprotein 39 (herein after referred to as HC gp-39) is a target autoantigen in RA patients which activates specific T cells, thus causing or mediating the inflammatory process. HC gp-39 derived peptides were predominantly recognized by autoreactive T cells from RA patients but rarely by T cells from healthy donors, thus indicating that HC gp-39 is an autoantigen in RA. The arthritogenic nature of HC gp-39 was further substantiated in the Balb/c mouse. A single, subcutaneous injection of said protein in Balb/c mice was able to initiate arthritic signs in the animals. The course of the HC gp-39-induced disease was characterized by relapses occuring periodically in fore paws and/or hind paws and gradually developed from a mild arthritis into a more severe form. Also, a symmetrical distribution of afflicted joints was observed which is, together with the observation of recurrent relapses and nodule formation, reminiscent of disease progression in arthritis, especially RA.

Even more surprisingly it was found that administration of HC gp-39 resulted in immunological tolerance and, more importantly, in delayed and/or suppressed arthritic development.

HC gp-39 is present in serum of both patients and healthy adults, although the serum concentration of the protein is about twice as much in patients as compared to healthy adults. Furthermore, mRNA coding for HC gp-39 can be found in synovial specimens or cartilage obtained from RA patients, whereas cartilage of healthy adults, obtained at surgery, does not contain a significant amount of said mRNA. When articular chondrocytes and synovial cells are cultured, their major secretory product becomes HC gp-39 (Hakala et al., J. Biol. Chem., Vol. 268, 34:25803, 1993). The arthritogenic nature of HC gp-39 was neither described nor suggested in the Hakala et al publication, nor in any other publication.

A further object of the invention is achieved by peptides comprising a subsequence of the autoantigen HC gp-39, characterized in that said peptides comprise one or more of the amino acid sequences FGRSFTLAS (SEQ ID No. 1), FTLASSETG (SEQ ID No. 2), YDDQESVKS (SEQ ID No. 3) and FSKIASNTQ (SEQ ID No 4).

More specifically, a peptide according to the invention comprises one or more of the amino acid sequences PTFGRSFTLASSE (SEQ ID No. 5), RSFTLASSETGVG (SEQ ID No. 6), VGYDDQESVKSKV (SEQ ID No. 7) and SQRFSKIASNTQSR (SEQ ID No. 8).

"Subsequence" is understood to be defined as "a part" and should not be mistaken to encompass the entire protein. Preferably the peptides according to the invention have an amino acid sequence of 9–55 amino acid residues. More preferably the peptides according to the invention have an amino acid sequence of 9–35, in particular 9–25 amino acid residues. Much more preferred are peptides having an amino acid sequence of 9–15 amino acid residues. Highly preferred are peptides having an amino acid sequence of 13 or 14 amino acid residues, such as for example peptides having the amino acid sequences given in SEQ ID No. 5–8.

Multimers of the peptide according to the invention, such as for example a dimer or a trimer, in which the monomer sequences optionally can be separated by spacer residues are also within the scope of the invention. Such multimers provide a multitude of the T cell epitopes given in SEQ ID No.'s 1–8.

BRIEF DESCRIPTION OF THE DRAWINGS

FIGS. 1A–1D show the initiation and progression of arthritis in HC gp-29 tolerized and non-tolerized Balb/c mice. In FIGS. 1A–1D, the number of animals that is afflicted as well as their total arthritis score are depicted on the Y-axis for both fore and hind paws; the X-axis represents the time after sensitization in days. Arthritis activity occurring in the fore paws of non-tolerized animals (FIG. 1A) was largely delayed and suppressed (FIG. 1B). Similarly, arthritis activity in the hind paws of these non-tolerized animals (FIG. 1C) was delayed and suppressed in mice that had been tolerized with HC gp-39 (FIG. 1D).

DETAILED DESCRIPTION OF THE INVENTION

Figure 1C:
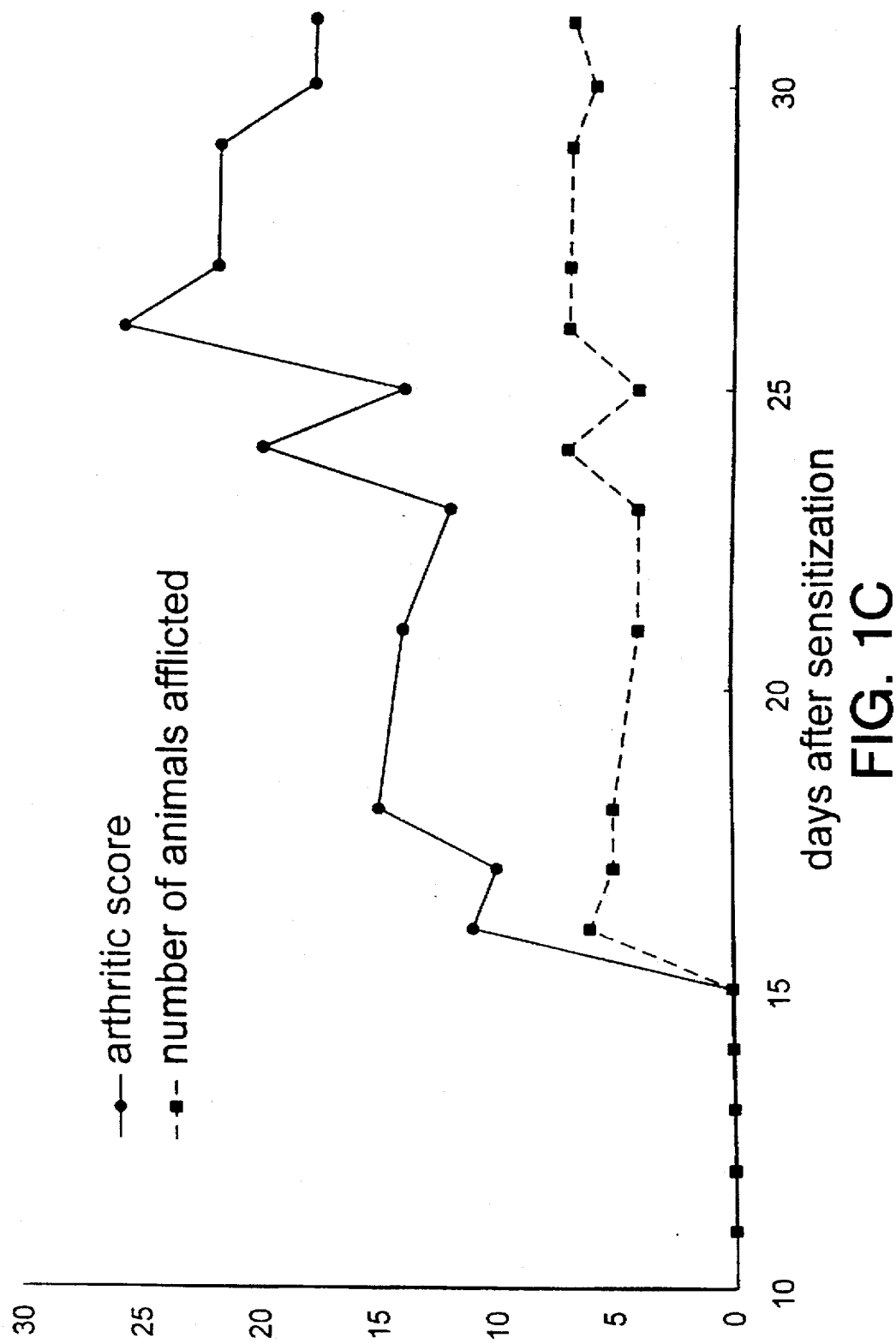

In the peptides according to the invention the amino acid sequences given in SEQ ID No. 1–8 can be flanked by flanking regions which may correspond to the native flanking sites of the corresponding amino acids in the amino acid sequence of the HC gp-39 protein or other proteins in which said amino acid sequences are present. Alternatively, said flanking regions can also be non-native amino acid sequences made up of random amino acid residues. These non-native flanking sites can be used to stabilize the peptides, thus increasing their biological availability. To increase the biological availability of the peptides according to the invention, non-native flanking sites are preferred.

The amino acid sequences given in SEQ ID No.'s 1–4, more specifically the sequences given in SEQ ID No.' 5–8 resemble MHC class II restricted T cell epitopes which are present on HC gp-39. MHC class II restricted T-cell epitopes on HC gp-39 are displayed by the regions 103–116, 259–271, 263–275 and 326–338 of the amino acid sequence of HC gp-39 (starting from the methionine in the signal sequence, see Hakala et al. 1993). Thus, according to the invention, the peptides can also be understood to encompass fragments of the autoantigen HC gp-39 which comprise one or more of the above identified MHC Class II restricted T-cell epitopes and they are also within the scope of the invention.

The peptides according to the invention are T-cell reactive peptides, which are recognized by and are able to stimulate activated, autoreactive T-cells. These autoreactive T cells are found in the blood of RA patients but rarely in healthy donors.

Thus, according to the invention HC gp-39 protein or the synthetic peptides, said peptides resembling the MHC Class II restricted T-cell epitopes present on the target autoantigen HC gp-39, are very suitable for use in a therapy to induce specific T-cell tolerance to HC gp-39 in patients suffering from T-cell mediated cartilage destruction, such as for example arthritis, more specifically rheumatoid arthritis.

WO 95/01995 and WO 95/02188 describe the diagnostic use of HC gp-39 as a marker for RA, the arthritogenic nature of HC gp-39 is neither disclosed nor suggested. Nowhere do they hint or suggest towards the use of HC gp-39, fragments thereof or T-cell reactive peptides according to the present invention in the antigen or peptide specific therapy to induce T-cell specific tolerance to the HC gp-39 in the cartilage under attack.

The preparation of the peptides according to the invention is effected by means of one of the known organic chemical methods for peptide synthesis. HC gp-39 and the peptides can also be prepared with the aid of recombinant DNA techniques.

The organic chemical methods for peptide synthesis are considered to include the coupling of the required amino acids by means of a condensation reaction, either in homogeneous phase or with the aid of a so-called solid phase.

The condensation reaction can be carried out as follows:

a) condensation of a compound (amino acid, peptide) with a free carboxyl group and protected other reactive groups with a compound (amino acid, peptide) with a free amino group and protected other reactive groups, in the presence of a condensation agent;

b) condensation of a compound (amino acid, peptide) with an activated carboxyl group and free or protected other reaction groups with a compound (amino acid, peptide) with a free amino group and free or protected other reactive groups.

Activation of the carboxyl group can take place, inter alia, by converting the carboxyl group to an acid halide, azide, anhydride, imidazolide or an activated ester, such as the N-hydroxy-succinimide, N-hydroxy-benzotriazole, p-nitrophenyl ester, N-hydroxy-benzotriazole ester or pentafluorophenyl ester.

The most common methods for the above condensation reactions are: the carbodiimide method, the azide method, the mixed anhydride method and the method using activated esters, such as described in The Peptides, Analysis, Synthesis, Biology Vol. 1–3 (Ed. Gross, E. and Meienhofer, J.) 1979, 1980, 1981 (Academic Press, Inc.).

Preparation of suitable fragments of above-mentioned peptides according to the invention using the "solid phase" is for instance described in J. Amer. Chem. Soc. 85:2149 (1963) and Int. J. Peptide Protein Res. 35:161–214 (1990). The coupling of the amino acids of the peptide to be prepared usually starts from the carboxyl end side. For this method a solid phase is needed on which there are reactive groups or on which such groups can be introduced. This can be, for example, a copolymer of benzene and divinylbenzene with reactive chloromethyl groups, or a polymeric solid phase rendered reactive with hydroxymethyl of amine-function.

A particulary suitable solid phase is, for example, the p-alkoxybenzyl alcohol resin (4-hydroxy-methyl-phenoxy-methyl-copolystrene-1% divinylbenzene resin), described by Wang (1974) J. Am. Chem. Soc. 95:1328. After synthesis the peptides can be split from this solid phase under mild conditions.

After synthesis of the desired amino acid sequence, detaching of the peptide from the resin follows, for example, with trifluoroacetic acid, containing scavengers, for example triisopropyl silane, anisole or ethanedithiol, thioanisol.

The reactive groups which may not participate in the condensation reaction are, as stated, effectively protected by groups which can be removed again very easily by hydrolysis with the aid of acid, base or reduction. Thus, a carboxyl group can be effectively protected by, for example, esterification with methanol, ethanol, tertiary butanol, benzyl alcohol or p-nitrobenzyl alcohol and amines linked to solid support.

Groups which can effectively protect an amino group are the ethoxycarbonyl, benzyloxycarbonyl, t-butoxy-carbonyl (t-boc) or p-methoxy-benzyloxycarbonyl group, or an acid group derived from a sulphonic acid, such as the benzene-sulphonyl or p-toluene-sulphonyl group, but other groups can also be used, such as substituted or unsubstituted aryl or aralkyl groups, for example benzyl and triphenylmethyl, or groups such as ortho-nitrophenyl-sulphenyl and 2-benzoyl-1-methyl-vinyl. A particularly suitable α-amino-protective group is, for example, the base-sensitive 9-fluorenyl-methoxycarbonyl (Fmoc) group [Carpino & Han (1970) J. Amer. Chem. Soc. 92:5748].

A more extensive account of possible protecting groups can be found in The Peptides, Analysis, Synthesis, Biology, Vol. 1–9 (Eds. Gross, Udenfriend and Meienhofer) 1979–1987 (Academic Press, Inc.).

The protective groups can be split off by various conventional methods, depending on the nature of the particular group, for example with the aid of trifluoroacetic acid or by mild reduction, for example with hydrogen and a catalyst, such as palladium, or with HBr in glacial acetic acid.

As already indicated above, HC gp-39 and the peptides according to the invention can likewise be prepared with the aid of recombinant DNA techniques. For this purpose, a nucleic acid sequence which codes for HC gp-39 or a peptide according to the invention or a multimer of said peptide is inserted into an expression vector. Suitable expression vectors are, amongst others, plasmids, cosmids, viruses and YAC's (Yeast Artificial Chromosomes) which comprise the necessary control regions for replication and expression. The expression vector can be brought to expression in a host cell. Suitable host cells are, for instance, bacteria, yeast cells and mammalian cells. Such techniques are well known in the art (Sambrook et al., Molecular Cloning: a Laboratory Manual, Cold Spring Harbor Laboratory Press, Cold Spring Harbor, 1989).

Although it seems paradoxical to desensitize the immune system with the very same antigen responsible for activating the immune system, the controlled administration of HC gp-39 and/or peptides comprising a subsequence of HC gp-39 can be effective in desensitization of the immune system. According to the invention, patients in which the cartilage is under attack of autoresponsive T cells can be treated with a pharmaceutical composition comprising HC gp-39, or one or more peptides according to the invention and a pharmaceutical acceptable carrier in order to make the specific autoreactive T cells of these patients tolerant to the HC gp-39 in the cartilage under attack and other self antigens carrying the identified T cell epitopes having one of the amino acid sequences given in SEQ ID No. 1–8 and to diminish the inflammatory response. Very suitable peptides to be used in a pharmaceutical composition according to the invention are the peptides having an amino acid sequence given in SEQ ID No. 5, 6, 7 and 8.

Also very suitable to be used in a pharmaceutical composition according to the invention are DNA (expression) vectors comprising DNA which encodes for HC gp-39 or one or more of the peptides according to the invention. Upon delivery the DNA (expression) vector can provide by expression a level of the recombinant HC gp-39 protein or peptides according to the invention which is similar to the level which would be achieved by direct administration of a pharmaceutical composition comprising the HC gp-39 protein or peptides.

The autoantigen and peptides according to the invention have the advantage that they have a specific tolerizing effect on the autoreactive T cells thus leaving the other components of the immune system intact as compared to the nonspecific suppressive effect of the immunosuppressive steroid drugs. Treatment with the autoantigen or peptides according to the invention will be safe and no toxic side effects will occur.

Tolerance can be attained by administering high or low doses of the autoantigen or peptides according to the invention. The amount of autoantigen or peptide will depend on the route of administration, the time of administration, the age of the patient as well as general health conditions and diet.

In general, a dosage of 0.01 to 1000 µg of peptide or protein per kg body weight, preferably 0.5 to 500 µg, more preferably 0.1 to 100 µg of peptide or protein can be used.

Pharmaceutical acceptable carriers are well known to those skilled in the art and include, for example, sterile salin, lactose, sucrose, calcium phosphate, gelatin, dextrin, agar, pectin, peanut oil, olive oil, sesame oil and water. Other carriers may be, for example MHC class II molecules, if desired embedded in liposomes.

In addition the pharmaceutical composition according to the invention may comprise one or more adjuvants. Suitable adjuvants include, amongst others, aluminium hydroxide, aluminium phosphate, amphigen, tocophenols, monophosphenyl lipid A, muramyl dipeptide and saponins such as Quill A. The amount of adjuvant depends on the nature of the adjuvant itself.

Furthermore the pharmaceutical composition according to the invention may comprise one or more stabilizers such as, for example, carbohydrates including sorbitol, mannitol, starch, sucrosedextrin and glucose, proteins such as albumin or casein, and buffers like alkaline phosphates.

Suitable administration routes are intramuscular injections, subcutaneous injections, intravenous injections or intraperitoneal injections, oral and intranasal administration. Oral and intranasal administration are preferred administration routes.

Due to its arthritogenic nature, HC gp-39 or the peptides according to the invention can be used to induce clinical arthritis in non-human mammalians. Upon administration of small amounts of HC gp-39 or one or more of the peptides according to the invention, arthritic signs will develop in said mammalians resulting in a disease pattern reminiscent of disease progression in arthritis, especially rheumatoid arthritis. When Balb/c mice were injected subcutaneously with HC gp-39 protein, the animals developed arthritic signs. This course of the HC gp-39-induced disease was characterized by relapses occuring periodically in fore paws and/or hind paws and gradually developed from a mild arthritis into a more severe form. Also, a symmetrical distribution of afflicted joints was observed which is, together with the observation of recurrent relapses and nodule formation, reminiscent of disease progression in arthritis, especially RA.

Thus, these afflicted animals provide an adequate animal model to study the mechanism underlying the initiation and progression of arthritic development. Additionally, said afflicted animals can be used to search for new drugs to treat arthritis and to study the effect of these drugs upon the arthritic development. Preferably mice are used as animal model for arthritis, especially rheumatoid athritis.

To induce arthritis in said mammalians, suitable amounts of HC gp-39 or one or more of the peptides according to the invention have to be administered. Suitable amounts are 0.1–1000 µg, preferably 1–100 µg, more preferably 10–50 µg per kg body weight. The amount of HC gp-39 or the peptides will depend on the route of adminstration, time of administration and the type of animal used. Suitable adminstration routes are the same as described before. To induce the effect of arthritis inducton, the HC gp-39 protein or peptides according to the invention may comprise one or more stabilizers or adjuvants as described before.

HC gp-39 or the peptides according to the invention are also very suitable for use in a diagnostic method to detect the presence of activated autoreactive T cells involved in the chronic inflammation of the articular cartilage.

The diagnostic method according to the invention comprises the following steps:

a) isolation of the peripheral blood mononuclear cells (PBMC) from a blood sample of an individual,
b) culture said PBMC under suitable conditions,
c) incubation of said PBMC culture in the presence of the autoantigen or one or more peptides derived thereof according to the invention, and
d) detection of a response of T cells, for example a proliferative response, indicating the presence of activated autoreactive T cells in the individual.

In case of detection of a response by measuring the proliferative response of the autoreactive T cells, the incorporation of a radioisotope such as for example $^3$H-thymidine is a measure for the proliferation. A response of the autoreactive T cells present in the PBMC can also be detected by measuring the cytokine release with cytokine-specific ELISA, or the cytotoxicity with $^{51}$Chromium release. Another detection method is the measurement of expression of activation markers by FACS analysis, for example of Il-2R. A diagnostic composition comprising one or more of the peptides according to the invention and a suitable detecting agent thus forms part of the invention. Depending on the type of dection, the detection agent can be a radioisotope, an enzyme, or antibodies specific for cell surface or activation markers.

Also within the scope of the invention are test kits which comprise one or more peptides according to the invention. These test kits are suitable for use in a diagnostic method according to the invention.

Thus, the present invention provides for a method to detect whether autoaggressive T cells reactive towards HC gp-39 are present in patients suffering from T-cell mediated cartilage destruction such as for example arthritis, in particular rheumatoid arthritis. If HC gp-39-specific T cells are present, tolerization of these T cells with a pharmaceutical compostion comprising HC gp-39 or peptides according to the present invention or combinations thereof can delay or suppress arthritis development.

The following examples are illustrative for the invention and should in no way be interpreted as limiting the scope of the invention.

LEGENDS TO THE FIGURES

Figure 1D:
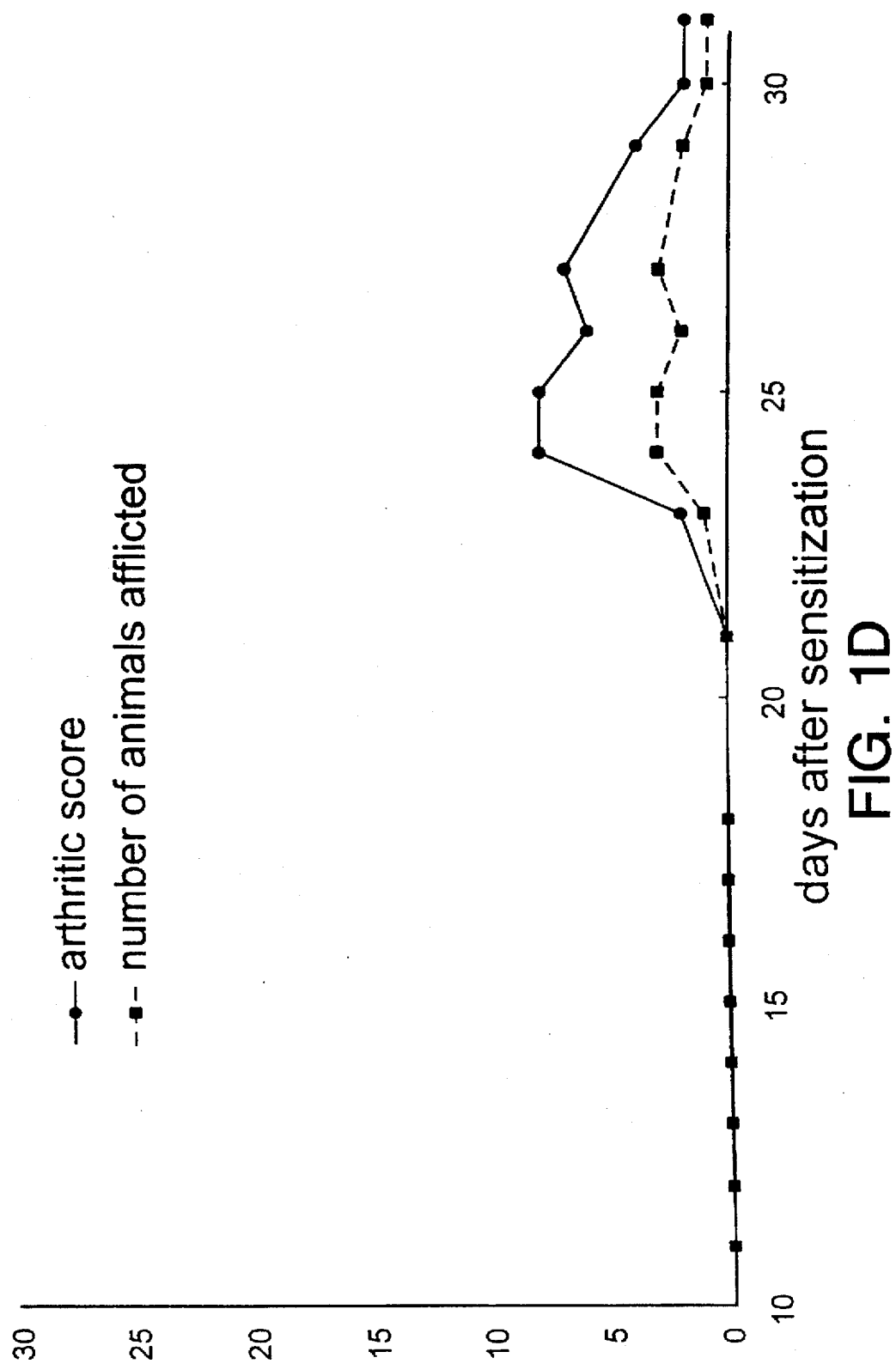

FIG. 1: Initiation and progression of arthritis in HC gp-39 tolerized and non-tolerized Balb/c mice. The total arthritic score of the afflicted animals per day following sensitization is given for both fore- and hind paw. The number of afflicted animals per day following sensitization is also given.

EXAMPLE 1

METHODS

Patients

Peripheral blood mononuclear cells (PBMC) from patients who were diagnosed as suffering from RA according to the American Rheumatism Association (ARA) criteria (Arnett et al., Arthritis Rheum. 31:315, 1988) were collected. The severity of disease of RA patients ranged from stage I–IV as determined by Röntgenscore.

PBMC's from healthy donors carrying the DR4Dw4 (DRB1*0401) or the DR1 specificity were collected as a control. Also PBMC's from two healthy donors who did not carry one of the RA associated DR molecules were collected.

MHC Typing

Patient and healthy donor PBMC chromosomal DNA extracts, were analysed using the Dynal DR 'low resolution' SSP kit. DR4 subtyping was performed using the Dynal DRB1*04-SSP kit (University Transfusion service, Radboud hospital, Nijmegen, The Netherlands).

Peptides

Peptides according to the invention and a control peptide were synthesized by solid-phase peptide synthesis. In brief, peptides with free amino- and carboxy termini were synthesized on a Milligen 9050 synthesizer, using Fmoc/tBu protected activated esters on PEG-PS resins. After cleaving off and deprotecting, the peptides were purified by preparative HPLC, converted into acetate salts with Dowex Ac-resin or into chloride salts and lyophilized. The peptides were checked with mass spectrometry. The peptides used in this study are listed in table 1. An N-terminal biotinylated Influenza Haemagglutinine derived peptide (SEQ ID No. 9), biotin-spacer-IHA(307–319)F, in which the third residue (Y) was replaced by F, (biotin-NH-$(CH_2)_5$-CO-PKFVKQNTLKLAT), was used as marker peptide in the binding studies with DR4Dw4 (DRB1*0401). The non-biotinylated peptide IHA(307–319)F having SEQ ID NO:9 was used as control peptide.

TABLE 1

The amino acid sequence of the synthesized peptides.

| peptide | sequence | HPLC purity | SEQ ID |
|---|---|---|---|
| 1 | PTFGRSFTLASSE | 93.2% | No. 5 |
| 2 | RSFTLASSETGVG | 85.6% | No. 6 |
| 3 | VGYDDQFSVKSKV | 95.6% | No. 7 |
| 4 | SQRFSKIASNTQSR | 97.6% | No. 8 |
| IHA(307-319)F | PKFVKQNTLKLAT | 97.9% | No. 9 |

The amino acid sequence of peptides 1–4 and the control peptide IHA(307-319)F are given, corresponding to the respective sequence ID's

Cell Culture for the Production of Purified HLA-DR Molecules

Two EBV-transformed B-cell lines, BSM (A2, B62, Cw3, DR4Dw4, DQ8, Dpw2) and BM92 (A25, B51, Cw1, DR4Dw14, DQ8), were a gift from the Academic Hospital Leiden, the Netherlands. The cells were cultured in DMEM/HAM's F12 (Gibco Laboratories, Grand Island, N.Y.) supplemented with 10% FCS (Hyclone Laboratories), 1% non-essential amino acids (ICI), L-glutamine, 2-ME and antibiotics. Cells were routinely passaged every 2–3 days in a 1:2 ratio. Cells were harvested and thereafter washed three times in PBS (4° C.) containing 1 mM PMSF. Cell pellets were stored at −70° C. until use.

Affinity Purification of HLA-DR Molecules

HLA-DR molecules were affinity purified from cell lysates using monoclonal antibody L243 (ATCC HB55), directed against a nonpolymorphic determinant on the DR-complex (Lampson et al., J. Immunol. 125:293, 1980). Protein G sepharose purified L243 was coupled to NHS-Sepharose 4 FF (Pharmacia) according to the manufactures instructions.

HLA-DR expressing cells were thawed and lysed on ice for 30 minutes in PBS, 1% NP-40, 1 mM AEBSF (Calbiochem). The lysate was cleared by centrifugation at 15.000 rpm (Sorvall, SS34 rotor) for 30 minutes. The supernatant was passed through a 0.45 μm filter and added to L243-NHS-sepharose beads. After overnight incubation, the beads were transferred to a column and washed with five volumes PBS, 1% NP-40; 5 volumes PBS, 0.5% NP-40; 15 volumes PBS, 0.5% NP-40, 0.1% SDS; 5 volumes PBS, 0.05% NP-40; 5 volumes PBS, 1% n-octyl-glucoside (Sigma, St. Louis, USA) and 5 volumes 50 mM diethylamine (Fluka), 150 mM NaCl, 1% n-octyl-glucoside pH=8.0. HLA-DR molecules were eluted with 50 mM diethylamine, 150 mM NaCl, 1% n-octyl-glucoside pH=11. Immediately after collection, the fractions were neutralised with 2M glycine pH=4.8. Collected fractions were analysed on SDS-PAGE under non-reducing conditions followed by silver staining. Fractions containing purified HLA-DR were concentrated by ultrafiltration over a 30 kD cut-off membrane.

HLA-DR Peptide Binding Assay

The peptide binding studies were performed using an improved version of a semi-quantitative binding assay described previously (Joosten et al., Int. Immunol. 6:751, 1994). Purified HLA-DR molecules (0.5–500 nM) were incubated at pH=5.0 with 50 nM biotinylated marker peptide (biotin-spacer-IHA(307–319)F) and a concentration range of competitor peptide (peptides 1–4 and IHA(307–319)F as a control peptide) in a final volume of 25 μl binding buffer (PBS, 1 mM AEBSF, 1 mM N-ethyl maleimide, 8 mM EDTA, 10 μM pepstatin A, 0.01% NaN$_3$, 0.05% NP-40 and 5% DMSO).

After approximately 45 hours incubation at room temperature, bound and unbound marker peptides were separated either by SDS-PAGE in combination with blotting on a nitrocellulose filter (BioRad) or by vacuum DOT blotting using a nitrocellulose filter (BioRad) and 96 wells Hybry Dot equipment (BRL). Blots were blocked with 0.5% DNA blocking reagent (Boehringer Mannheim, Germany) in 0.1M maleic acid pH=7.5, 150 mM NaCl. After ½ hour, blots were washed in PBS, 0.02% Tween 20 (Sigma, St. Louis, USA) and incubated with Streptavidin-HRPO (Southern Biotechnology) in a 1:40,000 or 1:5.000 dilution respectively. DR-bound, biotinylated marker peptide was detected by enhanced chemoluminescence using a Western Blot ECL kit (Amersham, U.K.) according to the manufactures instructions. Preflashed films (hyperfilm-ECL, Amersham, U.K.) were exposed for 10 minutes. The relative binding affinity of a given peptide was related to competition with the marker peptide. This relative affinity was defined as the peptide concentration at which the signal was reduced to 50% ($^R IC_{50}$).

In case of the SDS-PAGE, $^R IC50$ values were determined by visual inspection. The density of the DOT Blot-spots was analysed using a computing densitometer (Molecular Dynamics, USA) and IMAGE QUANT and EXCEL software.

Proliferative Responses of Blood Mononuclear Cells

In order to identify T cell reactivity to peptide sequences within HC gp-39, the peptides 1–4 were tested for their capacity to induce proliferative responses in PBMC from RA patients versus healthy DR1 or DR4 controls.

PBMC obtained from heparinized venous peripheral blood were isolated by standard centrifugation on a FICOLL-PAQUE gradient. Cells were cultured in three- or four-fold at a concentration of $1,5 \times 1.0^5$ cells/well in medium supplemented with 10% heat-inactivated autologous plasma, L-glutamine, 2-ME and antibiotics in flatbottomed microliter plates. Cells were incubated in medium alone or in the presence of PHA (2.5 μg/ml) or in the presence of antigens, including the *Candida albicans* extract (recall antigen) (1 μg/ml, 0.1 μg/ml) or one of the peptides 1–4 in concentrations of 100 μg/ml, 25 μg/ml or 10 μg/ml. Cultures were incubated in a total volume of 210 μl for 7 days at 37° C. in a humidified atmosphere of 5% CO$_2$. Cultures were pulsed during the last 18 hours with 0.25 μCi $^3$H-thymidine.

Definitions

Patients found to respond to both concentrations of at least one peptide tested were ranked as high responders (HR), patients found to respond to at least one of the concentrations of at least one peptide tested were ranked as responders (R). Consequently, patients which did not respond to any of the peptides tested were ranked as non-responders (NR).

The relative binding affinity of a given peptide was related to competition with the marker peptide. This relative affinity was defined as the peptide concentration at which the signal was reduced to 50% ($^R IC_{50}$).

RESULTS

In order to determine T cell reactivity to peptides 1–4, the PBMC proliferative response in RA patients and healthy donors was analyzed.

Sofar, most HR or R to the HC gp-39-derived peptides carried the DR1, DR4Dw4, DR4Dw14 or the DR10 specificity, all of which are known to be associated with an increased risk for the development of RA. Binding of the peptides 1–4 to DR4Dw4 and DR4Dw14 was demonstrated as shown in Table 2.

TABLE 2

Binding of the peptides 1-4 to HLA-DR molecules

| Peptide | DR4Dw4 SDS-PAGE | DR4Dw4 DOT Blot | DR4Dw14 SDS-PAGE | DR4Dw14 DOT Blot |
|---|---|---|---|---|
| 1 | 0.04 | 0.04 | 2.5 | 1.95 |
| 2 | 0.04 | 0.08 | 0.2 | 0.19 |
| 3 | 1 | 0.23 | >=50 | >10 |
| 4 | — | 0.08 | — | 0.4 |
| IHA(307-319)F | 0.3 | 0.55 | 0.3 | 0.53 |

Binding of peptides 1-4 having amino acid sequence given in SEQ ID No. 5-8 respectively to HLA-DR molecules. Peptide binding was determined in a semiquantitative binding assay (as described in Methods of Example 1) at pH = 5. using 50 nM IHA(307-319)F as a marker peptide. The values are $^RIC_{50}$ values in micromolar (concentration competitor peptide at which the signal is reduced to about 50% of the signal without competitor peptide). All results, except for peptide 4, are from two independent experiments (SDS-PAGE and DOT Blot, respectively).

Most RA patients responded to one or more of the peptides according to the invention (Table 3), whereas responses were rarely found in the healthy donor group (Table 4). 6 RA patient were found not to respond to any of the peptides tested (results not shown).

Disease severity in RA patients was ranked from stage I–IV. The röntgenscore as here indicated is an estimation of the degree of joint destruction. HR and R to the peptides 1–4 were found in all stages of disease.

The peptides according to the invention represent autoreactive T cell epitopes and reactivity to these epitopes was found predominantly in RA patients but rarely in healthy donors. Thus, RA patients have activated, autoreactive T-cells directed at the autoantigen HC gp-39. Clearly the autoantigen HC gp-39 is under attack of T-cells, resulting in inflammation and destruction of the HC gp-39 antigen in the cartilage.

TABLE 4

Proliferative responses of freshley isolated PBMC from healthy donors to peptides 1-4 measured in 10% autologous serum.

| Donor | Peptide 1 100 µg/ml | Peptide 1 10 µg/ml | Peptide 2 100 µg/ml | Peptide 2 10 µg/ml | Peptide 3 100 µg/ml | Peptide 3 10 µg/ml | Peptide 4 100 µg/ml | Peptide 4 10 µg/ml |
|---|---|---|---|---|---|---|---|---|
| 155-03 (NR) | 1 | 1 | 1 | 1 | 1 | <2 | | |
| 156-03 (NR | <2 | 2 | <1 | 1 | <1 | 1 | <2 | <1 |
| 157-03 (NR) | <2 | 1 | <2 | <2 | 1 | 1 | | |
| 157-04 (R) | — | 10 | <1 | 1 | — | 1 | 1 | 1 |
| 168-02 (NR) | 1 | <2 | <1 | <2 | <2 | <2 | | |
| 168-03 (NR) | <<1 | <2 | <1 | <1 | 1 | 1 | <1 | 1 |
| 169-02 (NR) | | | 1 | 1 | 1 | 1 | | |
| 230-01 (NR) | 1 | 1 | 1 | 1 | 1 | 1 | | |
| 235-0 (NR) | <2 | 1 | <2 | 1 | <2 | 1 | | |
| 235-01 (NR) | 1 | <2 | <1 | <1 | <2 | <1 | | |
| 236-01 (NR) | <1 | <1 | 1 | 1 | <1 | 1 | | |
| 237-0 (NR) | <1 | 1 | <1 | <2 | 1 | <1 | | |
| 237-01 (NR) | <<1 | <<1 | 1 | 1 | 1 | 1 | <1 | <1 |
| 238-0 (NR) | 1 | 1 | <1 | 1 | 1 | 1 | | |
| 238-01 (NR) | <1 | <1 | 1 | 1 | 1 | 1 | <1 | 1 |
| 241-0 (NR) | 1 | <2 | <1 | 1 | <1 | <1 | | |
| 241-01 (R) | 2 | <1 | <1 | <1 | 1 | <1 | <1 | <1 |

Proliferative responses of PBMC from healthy donors to peptides 1-4 having the amino acid sequences given in SEQ ID NO. 5-8 respectively. Results are presented as stimulation index (SI) values (= antigen-specific cp5m (mean of measurements)/control cp5m (mean of measurements)). SI values < 2 were regarded as negative. R = responder (+ respones at the highest peptide concentration tested) - = standard deviations of the mean of measurements exceeded acceptable values, therefor values are not given.

EXAMPLE 2

METHODS
Purification of HC gp-39 from the MG63 Osteosarcoma Cell Line

MG63 cells (human osteosarcoma ATCC CRL 1427) were cultured in cell factories in DMEM/HAM's F12 serum free medium. HC gp-39 was purified from the culture

TABLE 3

Proliferative responses of PBMC from RA patients to peptides 1-4 measured in 10% autologous serum.

| Patient | Peptide 1 100 µg/l | Peptide 1 25 µg/l | Peptide 1 10 µg/l | Peptide 2 100 µg/l | Peptide 2 25 µg/l | Peptide 2 10 µg/l | Peptide 3 100 µg/l | Peptide 3 25 µg/l | Peptide 3 10 µg/l | Peptide 4 100 µg/l | Peptide 4 25 µg/l | Peptide 4 10 µg/l | Disease state |
|---|---|---|---|---|---|---|---|---|---|---|---|---|---|
| 215-0 (HR) | 13 | 5 | | 19 | 3 | | 6 | 3 | | | | | III–IV |
| 240-0 (HR) | 9 | 5 | | 6 | 5 | | 6 | 2 | | | | | II–III |
| 242-0 (HR) | — | 9 | | — | 4 | | 3 | 9 | | | | | I |
| 243-0 (R) | 2 | | <1 | 6 | | 1 | 1 | | 1 | | | | III |
| 247-0 (R) | 9 | | 1 | 2 | | 1 | — | | 1 | | | | III |
| 248-0 (R) | 2 | | 1 | 1 | | 1 | 1 | | 1 | | | | III |
| 191-03 (HR) | 3 | | 2 | <2 | | 1 | <2 | | 1 | <2 | | <2 | IV |
| 272-0 (R) | <2 | | 1 | <1 | <1 | <1 | <1 | | <1 | 6 | | <2 | III–IV |
| 273-0 (HR) | 14 | | 12 | 6 | | 7 | 6 | | 1 | 29 | | 3 | IV |
| 275-0 (HR) | 2 | | 4 | 9 | | 2 | 1 | | 1 | 5 | | <2 | III |
| 276-0 (HR) | 4 | | 3 | 1 | | 3 | 1 | | <1 | <2 | | 1 | IV, burnt out |
| 280-0 (HR) | 11 | | 6 | 4 | | 1 | 1 | | 1 | 2 | | <2 | IV, burnt out |

Proliferative responses of PBMC from RA patients to the peptides 1-4 with the amino acid sequence given in SEQ ID No. 5-8 respectively. Results are presented as stimulation index (SI) values (= antigen-specific cp5m (mean of measurements)/control cp5m (mean of measurements)). Cp5m = counts per 5 minutes. SI values ≧ were regarded as positive, SI values < 2 as negative. — = standard deviations of the mean of measurements exceeded acceptable values, therefore values are not given. HR = high responder (+ responses at both peptide concentrations tested), R = responder (+ responses at the highest peptide concentration tested). Burnt out = almost all cartilage has disappeared.

supernatant by heparin affinty chromatography followed by super dex 75 chromatography. Purity was checked by SDS-PAGE. In addition, N-terminal amino acid sequencing confirmed that the purified protein was identical to the protein described by Hakala et al.

Arthritogenicity of HC gp-39 in Balb/c Mice 10 or 50 µg of purified HC gp-39 in a 100 µl volume PBS (0.5M NaCl, 0.01M sodium phosphate buffer, pH 7.5) mixed 1:1 in incomplete Freunds adjuvant (IFA) was injected subcutaneously in the chest region in 2×4 female Balb/c mice (Harlan CPB, Zeist, The Netherlands) whereas 4 controls were injected with PBS (1:1 in IFA). Mice were examined daily for clinical signs of arthritis. Severity of arthritis was assessed by scoring each paw from 0–3 (according to the article by Glant et al). In short, score 0=no changes, score 1=erythema and swelling, score 2=swelling and appearance of deformities, score 3=immobility due to loss of flexion and extension.

Tolerance Induction by Intranasal Administration of HC gp-39

Twenty eight µg of protein was administered intranasally (2×10 µl) to 10 female Balb/c mice (anesthetized lightly with Enflurance) using a PT45 micro conduit and a Hamilton syringe. Antigen was administered on day -15, -10 and -5 prior to arthritis induction. Controls (n=10) were submitted to the same procedure but recieved the vehicle (PBS) only (Table 5).

Immunological tolerance was evaluated by measuring delayed type hypersensitivity (DTH) responses following sensitization as described above on day 0, using 10 µg of protein. Sensitization on day 0 was followed by an injection of 10 µg HC gp-39 in 50 µg volume in the left hind footpad on day 8 (challenge). DTH reactions were measured as the increase in footpad ([swelling left (mm×10$^{-3}$)–swelling right (mm×1$^{-3}$)]/swelling right (mm×10$^{-3}$))×100%. The footpad swelling was measured using an inhouse designed µmeter at 0, 24 and 48 hr after challenge.

Tolerance to arthritis induction in these same mice was then further monitored until day 31 following sensitization and mice were examined daily for clinical signs. Severity of arthritis was assessed as mentioned above.

TABLE 5

| | Tolerization scheme. | |
| --- | --- | --- |
| DAY | HC gp-39 tolerized | non-tolerized |
| -15 | 28 µg HC gp-39 intra nasal | PBS |
| -10 | 28 µg HC gp-39 intra nasal | PBS |
| -5 | 28 µg HC gp-39 intra nasal | PBS |
| 0 | 10 µg HC gp-39 subcutaneous | 10 µg HC gp-39 subcutaneous |
| 8 | 10 µg HC gp-39 footpad | 10 µg HC gp-39 footpad |
| 9 | 24 hour DTH | 24 hour DTH |
| 10 | 48 hour DTH | 48 hour DTH |
| 0-31 | score arthritic signs | score arthritic signs |

DTH = delayed type hypersensitivity. PBS = 0.5 NaCl, 0.01 M. sodium phosphate buffer, pH 7.5

RESULTS

Arthritogenicity of HC gp-39

Following one injection of 50 µg HC gp-39 mixed with IFA, all mice gradually developed a severe arthritis (Table 6). Signs of arthritis were observed first at day 15–20 after sensitization, in the fore paws of 3 out of 4 animals. The mouse that did not show any signs in the fore paws developed arthritis in the hind paws by day 34 upon sensitization. The course of HC gp-39-induced disease was characterized by relapses occuring periodically in fore paws or hind paws and gradually develloped from mild arthritis into a more severe arthritis (disease progression was followed for 62 days). Very often (>50%) a symmetrical distribution of afflicted joints was observed, meaning that both fore paws or both hind paws showed arthritic signs at the same time.

Arthritis induction was similarly achieved using 10 µg instead of 50 µg HC gp-39 mixed with IFA. Arthritic scores, however, were somewhat lower (data not shown). Three out of 4 mice developed a severe arthritis. One mouse showed only mild signs during the duration of the experiment. All through the length of the experiment control mice showed no signs of arthritis.

In aggregate, both 10 and 50 µg of protein were sufficient to induce a progressive arthritis in Balb/c mice. The chronic nature of arthritis induction by HC gp-39, characterized by recurrent relapses in addition to symmetrical affliction of joints is reminiscent of disease progression in rheumatoid arthritis (RA).

TABLE 6

Initiation and progression of arthritis in HC gp-39 sensitized Balb/c mice.

| sensitization | arthritis onset (day) | | arthritis signs | | |
| --- | --- | --- | --- | --- | --- |
| (n = 4) | HP | RP | none | mild | severe |
| PBS contr. | — | — | 4 | 0 | 0 |
| 10 µg HC gp-39 | —, 13, 15, 57 | 32, 34, 36, 43 | 0 | 1 | 3 |
| 50 µg HC gp-39 | 13, 15, 15, 48 | 29, 34, 34, 53 | 0 | 0 | 4 |

FP = fore paw. HP = hind paw. contr. = controls. Arthritis signs: none: score = 0, mild: score per animal does not exceed 2, severe: score per animal is ≧ 4.

Immunological Tolerance Measured in the DTH Assay

Control mice injected with HC gp-39 at day 0 showed a strong, antigen-specific DTH response, which suggests that a cellular immune response to HC gp-39 was elicited upon sensitization (Table 7). Intranasal administration of HC gp-39, however, completely abrogated DTH responses upon challenge with the autoantigen, thereby showing that the HC gp-39-specific T-cells were indeed tolerized.

Notably, 4 out of 10 animals of the non-tolerized group developed arthritis in the ankle adjacent to the site of challenge. In contrast, the tolerized group did not develop an arthritis in the joints neighbouring the challenged site, thereby suggesting that immunological tolerance to HC gp-39 results in protection against arthritis development.

TABLE 7

DTH responses to HC gp-39 following tolerization by nasal administration.

| | mean % swelling | | | |
| --- | --- | --- | --- | --- |
| treatment | 0 hr | 24 hr | 48 hr | arthritis ankle |
| controls(n = 10) | -1.3 | 31.4 | 38.6 | 4/10 |
| tolerized(n = 9) | -0.05 | 3.7 | 1.5 | 0/9 |

Tolerance to Arthritis Induction or Progression

The HC gp-39 tolerized and the non-tolerized Balb/c mice were then further monitored for initiation and progression of arthritis.

In all mice of the control (non-tolerized) group, disease was initiated upon sensitization with HC gp-39 (Table 8). Seven mice gradually developed a severe arthritis whereas three mice showed only mild signs (highest score 2). In contrast, five mice of the HC gp-39-tolerized group were protected against disease development during the course of the experiment. Furthermore, two animals of the tolerized group showed only mild signs for brief periods of time. Three animals developed a more severe arthritis with scores of 4.

Interestingly, in tolerized animals, arthritis onset was delayed in both hind and fore paws by a minimum of 7–9 days respectively (FIG. 1). Although fewer animals were affected in the tolerized group, the arthritic score per animal of the fore paws was comparabe to the arthritic score in the non-tolerized animals. The arthritic score per animal of the hind paws however, was somewhat lower in the tolerized animals (FIG. 1).

TABLE 8

Initiation and progression of arthritis in HC gp-39-tolerized and non-tolerized Balb/c mice.

| animals | arthritis onset (day) | arthritis signs | | |
|---|---|---|---|---|
| | | none | mild | severe |
| controls(n = 10) | 13–16 | 0 | 3 | 7 |
| tolerized (n = 10) | 23–24 | 5 | 2 | 3 |

Onset arthritis: first signs appear - highest number of animals affected. Arthritis signs: no signs: score = 0, mild: score per animal does not exceed 2, severe: score per animal is ≧ 4.

The experiments above demonstrate the arthritogenic nature of HC gp-39 in Balb/c mice. The course of HC gp-39-induced disease was characterized by relapses occurring periodically in fore paws and/or hind paws and gradually developed from a mild arthritis into a more severe form. Also, a symmetrical distribution of afflicted joints was observed which is together with the observation of recurrent relapses, reminiscent of disease progression in rheumatoid arthritis. The fierce arthritogenic nature of HC gp-39 was illustrated by a single, subcutaneous injection of 10 or 50 μg of protein which initiated arthritic signs in all animals. That HC gp-39 specific T cells are indeed elicited in response to HC gp-39 sensitization was shown by induction of HC gp-39-specific DTH responses. These data were further confirmed by the demonstration of HC gp-39-specific in vitro proliferative responses in animals immunized in the footpad with HC gp-39 (data not shown). Importantly, non-tolerized animals developed arthritis in the ankle neighbouring the injection site, thereby indeed suggesting an involvement of HC gp-39-specific T cells in arthritis induction.

Intranasal administration of peptide antigen has been used to induce antigen-specific immune tolerance. The experiments showed that intranasal administration of HC gp-39 leads to immunological non-responsiveness. DTH responses following sensitization were completely abrogated in HC gp-39-tolerized mice whereas control mice showed an antigen-specific swelling. These observations indicate that adminstration of HC gp-39 leads to peripheral immune tolerance.

In non-tolerized animals DTH responses were accompanied by arthritis in the ankle (adjacent to the challenged site) in four out of ten mice. In contrast, the ankles of HC gp-39-tolerized animals were indeed fully protected, thereby suggesting that autoreactive T-cells have been effectively silenced. The notion that tolerization with HC gp-39 protects against disease developement was taken further by the observation that 5 out of 10 animals in the tolerized group were entirely protected throughout the length of the experiment. Although the other five animals in the group did eventually develop clinical signs, the onset of arthritis was considerably delayed. Hence it can be concluded that HC gp-39-specific T cells are involved in the arthritogenic process and more importantly, that by tolerization of these T cells with a pharmaceutical composition according to the present invention arthritis development can be delayed or suppressed.

---

We claim:

1. A peptide of HC (human cartilage) gp-39, said peptide having 9–55 amino acid residues and comprising one or more of the amino acid sequences FGRSFTLAS (SEQ ID NO:1), FTLASSETG (SEQ ID NO:2), YDDQESVKS (SEQ ID NO:3) FSKIASNTQ (SEQ ID NO:4), PTFGRSFT-LASSE SEQ ID NO:5), RSFTLASSETGVG (SEQ ID NO:6), VGYDDQESVKSKV (SEQ ID NO:7) and SQRF-SKIASNTQSR (SEQ ID NO:8), wherein said peptide will stimulate autoreactive T cells found in the blood of rheumatoid arthritis patients which are reactive with HC gp-39.

2. The peptide according to claim 1 having the amino acid sequence PTFGRSFTLASSE (SEQ ID NO:5).

3. The peptide according to claim 1 having the amino acid sequence RSFTLASSETGVG (SEQ ID NO:6).

4. The peptide according to claim 1 having amino acid sequence VGYDDQESVKSKV (SEQ ID NO:7).

5. The peptide according to claim 1 having amino acid sequence SQRFSKIASNTQSR (SEQ ID NO:8).

6. A pharmaceutical composition comprising an effective amount of one or more of the peptides according to claim 1, and a pharmaceutically acceptable carrier.

7. A composition comprising one or more of the peptides according to claim 1, and a detection agent.

8. A diagnostic method for the detection of activated autoreactive T cells which are reactive with HC gp-39, comprising the following steps:

a) isolating peripheral blood mononuclear cells (PBMC) from a blood sample of an individual, b) culturing said PBMC under suitable conditions, c) incubating said PBMC culture in the presence of HC gp-39, fragments thereof and/or one or more peptides according to claim 1, and d) detecting a response of T cells, indicating the presence of activated autoreactive T cells in the individual.

9. A test kit for the detection of activated autoreactive T cells which are reactive with HC gp-39, said test kit comprising one or more of the peptides according to claim 1.

10. A method for treating a patient with rheumatoid arthritis said patient having T cells which are reactive with HC gp-39, comprising administering a desensitizing amount of HC gp-39, and/or a peptide according to claim 1 to the patient.

\* \* \* \* \*

SEQUENCE LISTING ( 1 ) GENERAL INFORMATION:

( i i i ) NUMBER OF SEQUENCES: 9

( 2 ) INFORMATION FOR SEQ ID NO: 1:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 1:

Phe  Gly  Arg  Ser  Phe  Thr  Leu  Ala  Ser
    1                        5

( 2 ) INFORMATION FOR SEQ ID NO: 2:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 2:

Phe Thr Leu Ala Ser Ser Glu Thr Gly
1               5

( 2 ) INFORMATION FOR SEQ ID NO: 3:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 3:

Tyr Asp Asp Gln Glu Ser Val Lys Ser
1               5

( 2 ) INFORMATION FOR SEQ ID NO: 4:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 4:

Phe Ser Lys Ile Ala Ser Asn Thr Gln
1               5

( 2 ) INFORMATION FOR SEQ ID NO: 5:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 5:

Pro Thr Phe Gly Arg Ser Phe Thr Leu Ala Ser Ser Glu
1               5                   10

( 2 ) INFORMATION FOR SEQ ID NO: 6:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 6:

Arg Ser Phe Thr Leu Ala Ser Ser Glu Thr Gly Val Gly
1               5                   10

( 2 ) INFORMATION FOR SEQ ID NO: 7:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 7:

```
Val Gly Tyr Asp Asp Gln Glu Ser Val Lys Ser Lys Val
1               5                   10
```

( 2 ) INFORMATION FOR SEQ ID NO: 8:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 8:

```
Ser Gln Arg Phe Ser Lys Ile Ala Ser Asn Thr Gln Ser Arg
1               5                   10
```

( 2 ) INFORMATION FOR SEQ ID NO: 9:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 9:

```
Pro Lys Phe Val Lys Gln Asn Thr Leu Lys Leu Ala Thr
1               5                   10
```